United States Patent
Flynn et al.

(10) Patent No.: US 7,309,316 B1
(45) Date of Patent: Dec. 18, 2007

(54) MAGNETIC NEEDLE BIOPSY

(76) Inventors: Edward R. Flynn, 11109 Country Club Dr. NE., Albuquerque, NM (US) 87111; Richard Larson, University of New Mexico Cancer Research Facility, Room 223A, Albuquerque, NM (US) 87131

( * ) Notice: Subject to any disclaimer, the term of this patent is extended or adjusted under 35 U.S.C. 154(b) by 158 days.

(21) Appl. No.: 11/069,361

(22) Filed: Feb. 28, 2005

Related U.S. Application Data

(60) Provisional application No. 60/549,501, filed on Mar. 1, 2004.

(51) Int. Cl.
*A61B 10/00* (2006.01)

(52) U.S. Cl. ...................................... 600/562

(58) Field of Classification Search ................ 600/562
See application file for complete search history.

(56) References Cited

U.S. PATENT DOCUMENTS

| | | | | |
|---|---|---|---|---|
| 4,018,886 | A * | 4/1977 | Giaever | 436/526 |
| 4,161,943 | A * | 7/1979 | Nogier | 600/12 |
| 4,346,715 | A * | 8/1982 | Gammell | 607/99 |
| 4,508,119 | A * | 4/1985 | Tukamoto | 606/189 |
| 4,574,782 | A * | 3/1986 | Borrelli et al. | 600/10 |
| 4,590,922 | A * | 5/1986 | Gordon | 600/10 |
| 4,675,286 | A * | 6/1987 | Calenoff | 435/7.21 |
| 4,735,796 | A * | 4/1988 | Gordon | 424/9.32 |
| 4,829,984 | A * | 5/1989 | Gordon | 600/12 |
| 5,043,101 | A | 8/1991 | Gordon | |
| 5,067,952 | A | 11/1991 | Gudov et al. | |
| 5,203,782 | A * | 4/1993 | Gudov et al. | 606/31 |
| 5,486,161 | A * | 1/1996 | Lax et al. | 604/22 |
| 5,715,837 | A * | 2/1998 | Chen | 128/899 |
| 5,735,279 | A | 4/1998 | Klaveness | |
| 5,738,837 | A | 4/1998 | Klaveness et al. | |
| 5,782,764 | A * | 7/1998 | Werne | 600/411 |
| 5,935,123 | A * | 8/1999 | Edwards et al. | 606/41 |
| 6,203,487 | B1 * | 3/2001 | Consigny | 600/12 |
| 6,400,980 | B1 * | 6/2002 | Lemelson | 600/478 |
| 6,459,924 | B1 * | 10/2002 | Creighton et al. | 600/427 |
| 6,660,002 | B1 * | 12/2003 | Edwards et al. | 606/41 |
| 6,958,062 | B1 * | 10/2005 | Gough et al. | 606/41 |
| 6,960,196 | B2 * | 11/2005 | Prindle | 604/272 |
| 6,997,863 | B2 * | 2/2006 | Handy et al. | 600/9 |

* cited by examiner

*Primary Examiner*—Max F. Hindenburg
*Assistant Examiner*—Jonathan Foreman
(74) *Attorney, Agent, or Firm*—Janeen Vilven-Doggett; Peacock Myers, P.C.

(57) ABSTRACT

An apparatus and method for performing biopsies in-vivo using magnetically labeled nanoparticles is disclosed. One embodiment of the apparatus is called a magnetic needle. When used in a biopsy, one embodiment of the present invention collects cancer cells in-vivo which have been tagged with magnetic nanoparticles coated with antibodies for specific cancer or tumor cells.

18 Claims, 5 Drawing Sheets

MAGNETIC NEEDLE BIOPSY

CROSS-REFERENCE TO RELATED APPLICATIONS

This application claims the benefit of the filing of U.S. Provisional Patent Application Ser. No. 60/549,501, entitled "Magnetic Needle Biopsy", filed on Mar. 1, 2004, and the specification thereof is incorporated herein by reference.

BACKGROUND OF THE INVENTION

Field of the Invention (Technical Field)

The present invention relates generally to methods and apparatus for recovering biopsy material, such as bone marrow, bone, and contiguous tissue, from a patient and subsequent collection and storage.

Biopsies are a painful procedure that often have to be repeated a number of times and in several places to achieve sufficient sample for detection of cancer cells. This is particularly true of bone marrow biopsies. In addition, the sensitivity and specificity of the procedure is low in most clinical scenarios.

Bone marrow biopsies consists of puncturing the bone in the iliac crest (pelvis), and obtaining an aspiration of liquid marrow through the hollow needle, followed by a core needle biopsy, which is obtained by breaking off a piece of bone with back and forth, and side to side, movements of the core needle. This procedure is used for diagnostic purposes, for staging patients with various malignancies, and for determining if treated patients have any residual cancer after therapy.

Information from the bone marrow biopsy informs the course of the patient's treatment. Patients with acute leukemia are treated with chemotherapy to put them into remission. There are prognostic variables found prior to treatment that help physicians determine these patients general prognosis and thus tailor their therapy. Thus patients with good prognostic variables may receive less aggressive chemotherapy and still achieve an excellent cure rate.

A bone marrow examination is the generally accepted standard of practice to evaluate malignancy. Morphologic review by light microscopy of bone marrow biopsies has a significant false negative rate between (1-50%) depending on the tumor and tissue type. The false negative rate is the result of two primary factors: 1.) appropriate and adequate sampling of the marrow, and 2.) identification of the tumor cells in the sample. The latter problem has substantially contributed to the false negative rate, but with the advent of polymerase chain reaction, immunoperoxidase staining, and flow Cytometry, the sensitivity of detecting a tumor cell has improved from 1 in 100 to upwards of 1 in $10^3$-$10^6$ cell in many scenarios.

Sampling technology has not changed for over 40 years and the manual bone marrow biopsy has remained essentially unchanged. The ability to adequately sample the bone marrow space is confounded by two major considerations: 1.) The bone marrow space in human adults has several trillion cells, of which approximately 10-50 million are sampled, and 2.) many disease processes do not diffusely infiltrate the marrow space, but occur in multiple foci.

There is growing evidence that an important prognostic indicator is the rate at which patients go into remission. That is, patients achieving a rapid clearance (i.e. negative bone marrow biopsy 14 days after initial chemotherapy) of their leukemia are found to do better than patients who achieve remission over a longer period of time. This has been noted in both acute lymphocytic leukemia, and acute myelocytic leukemia.

However, there are patients who have negative bone marrow biopsies who do poorly, in part due to false negative sampling. Samples from day 14 marrows have very low cellularity due to chemotherapy treatment (less than 1 million cells in many cases). A technology that could increase the sampling of cells without increasing the number of biopsies performed could potentially decrease false negative reports. In addition, proliferation of normal cells (i.e. Hematogones) that morphologically appear as blasts can further confound light microscopy interpretation, and the lack of cells can mitigate adequate evaluation by PCR.

Breast cancer is a common malignancy. There are a number of variables that can be used to assess a patients' prognosis and thus tailor therapy. These include the size and grade of the tumor, and the lymph node status. Recent studies have demonstrated that finding breast cancer cells in a bone marrow biopsy/aspirate performed at the time of the mastectomy has significant prognostic value. Breast cancer commonly invades the marrow in small microscopic foci that may not be sampled with traditional "one pass" bone marrow biopsy. Obtaining biopsy samples through the use of embodiments of the present invention would greatly increase the effective sampling of a biopsy sites such as bone marrow or solid tumor by having the target of interest drawn to the needle rather than having the needle sample the tumor cells. This results in an enriched sample. A biopsy apparatus and method providing for an enriched sample will increase sampling sensitivity and will result in a more effective prognosis and course of action.

Patients with various forms of leukemia, lymphoma and myeloma are treated with autologous hemapoetic stem cell transplants (HSCT). In this procedure, hemapoetic stem cells (HSC) isolated from the patient are reinfused after the patient is subjected to high dose chemotherapy/radiation therapy. Although effective in a number of patients, it has been long recognized that the HSCs can be contaminated with tumor cells. Thus the relapse of the tumor can in some cases be due to this contamination, despite the tumor being eradicated from the patient prior to the reinfusion of the HSC. A number of assays to detect these tumor cells are employed.

The use of magnetic nanoparticles with appropriately-labeled antibodies to target certain specific types of cancer, drug separation and the use of RF heating of magnetic particles for hyperthermia treatment is known (U.S. Pat. Nos. 5,735,279; 5,738,837; 5,043,101; 6,459,924; 5,067,952; 5,203,782; and Proceedings of the Scientific and Clinical Applications of Magnetic Carriers (Hafeli, Urs, Schutt, W., Teller, J., Zborowski, M., (eds.), Plenum Press, NY, 1997; Hafeli, U., Zbrowoski, M., (Eds.) J. Magn. Magn. Mater. 194, 1999; Hafeli, U., Zbrowoski, M., (Eds.), J. Magn. Magn. Mater. 225, 2001). There is a large range of antibodies known for numerous cancer types such as leukemia, breast, prostate, and Hodgkin's disease. There are also known neo-vascular agents, toxins and chemicals that can be attached to magnetic nanoparticles for seeking out tumors, and delivering a compound that will cause harm to the cancer cell.

The magnetic nanoparticles of primary interest are superparamagnetic rather than ferromagnetic providing the important advantages of not attracting each other when not in the presence of an external field and do not form clusters. Superparamagnetic particles exhibit magnetic properties similar to paramagnetic particles in the absence of a magnetic field but have ferromagnetic characteristics such as susceptibilities of many thousands, when in a magnetic field. Exposure to magnetic fields polarize the particles along the field lines and the particles will follow magnetic force lines in a non-uniform magnetic field. Through cell adhesion by antibody action, this force will pull the cell with it. The nano scale interaction between labeled nanoparticles and target can improve the efficiency of biopsies in both bone marrow, solid tumors and serum and reduce the number of biopsies required while increasing the specificity of cancer cell detection.

Magnetic guidance of needle biopsy has previously been disclosed by others. Magnetic guidance results in guiding catheters to the brain and heart to treat blood vessels in the brain and heart. The magnetic guidance method is based on using external electromagnetic coils to move magnetic material wires through blood vessels. The movement is guided by CAT scan imaging and computer control of the force fields exerted by the coils on the wire.

Such advances in the staging of various solid tumors has been led by the advent of CAT scans and more recently PET scans. Patients with a localized tumor often are found to have a small suspicious nodule in a metastatic site and it confirmation is required to determine if these metastatic nodules are malignant for decisions on the correct treatment. It is currently routine clinical practice to biopsy these lesions, often by a CAT scan guided needle biopsy.

Systems and methods previously disclosed have the disadvantage that they do not use magnetic nanoparticles to identify distant tumor/cancer cells by magnetic extraction nor do they have the capability of directly treating these sites with introduction of anti-cancer agents.

BRIEF SUMMARY OF THE INVENTION

According to one embodiment of the present invention, a magnetic biopsy apparatus for collecting a tissue sample from a subject comprises a cannulae having openings at the distal end and proximal end. The cross-sectional area in between the distal end and the proximal end is substantially hollow. The cannulae is suitable for accepting paramagnetic or superparamagnetic nanoparticles for injecting into a biopsy site. The cannulae accepts a magnetizable rod capable of being inserted into and retracted from the cannulae. The magnetizable rod having a distal end and a proximal end.

According to another embodiment of the present invention, a method of obtaining a tissue biopsy sample is described. Paramagnetic or superparamagnetic nanoparticles are injected into a biopsy site through a biopsy cannulae. A rod capable of being magnetized through the cannulae is placed into or near the biopsy site. The rod is magnetized. The superparamagnetic nanoparticles in or near the environment of the biopsy site are collected onto the magnetized rod. The magnetized rod with the paramagnetic or superparamagnetic nanoparticles attached thereto is removed from the cannulae. The paramagnetic or superparamagnetic nanoparticles are collected for analysis.

One aspect of the present invention improves the efficacy of biopsies by reducing the number of biopsies required to determine the presence of cancer and improving the efficiency and specificity.

Another aspect of the present invention improves the identification and isolation of these cells and thus enhance the sensitivity of these tests.

Another aspect of the present invention allows for the biopsy and treatment of distant sites including tumors, cancers, and serum. According to one embodiment of the present invention, this is accomplished through the use of magnetic guidance of the magnetic needle using external magnetic fields controlled by computers.

One aspect of the present invention provides improved efficiency and specificity of biopsies. Yet another aspect of the present invention improves the sensitivity of biopsies but are less invasive and painful.

BRIEF DESCRIPTION OF THE SEVERAL VIEWS OF THE DRAWINGS

FIG. 2a illustrates a magnetic biopsy device comprising a guidance tube with a central needle containing a stainless steel rod and a magnetic tip on the end of the rod wherein the magnetic tip ranges in size from one (1) cm to five (5) cm in length according to one embodiment of the present invention.

FIG. 2b illustrates a magnetic biopsy device comprising a guidance tube with a ferrous needle attached at one end to a strongly magnetized material according to one embodiment of the present invention.

FIG. 2c illustrates a magnetic biopsy device comprising a guidance tube with a ferrous material attached at one end in addition to a strong electromagnet attached thereto according to one embodiment of the present invention.

DETAILED DESCRIPTION OF THE INVENTION

Figure 1:
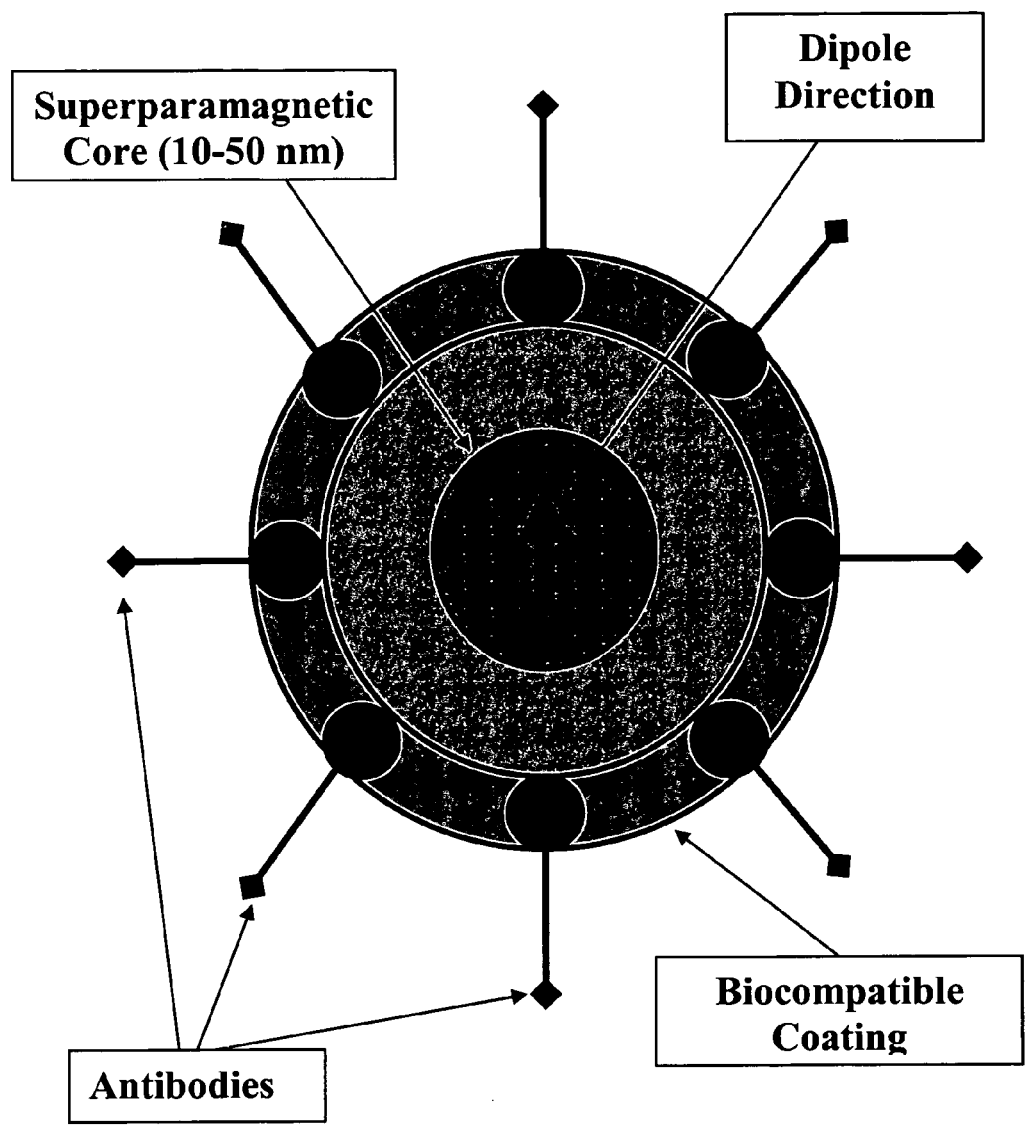
FIG. 1 is a graphical illustration of a magnetic nanoparticle which contains a ferrite core, a coating of a biocompatible material, and a coating of specific antibodies according to one embodiment of the present invention.

According to one embodiment of the present invention, a needle assembly is similar to a standard biopsy needle with a central shaft and a thin-walled cylindrical channel surrounding the shaft. According to another embodiment of the present invention, a magnetic biopsy device is inserted into the biopsy site, the central piercing shaft is removed and antibody-coated superparamagnetic nanoparticles are injected into the site. Subsequently, a magnetizable rod is inserted into the biopsy channel, a magnetic pole is induced within the rod and magnetically tagged cells are attracted to the rod. The rod with the magnetically tagged cells are removed from the site for analysis. The magnetic biopsy apparatus does not require general tissue or marrow samples but specifically collects cells of interest. Bone marrow biopsies are one area of application. Embodiments of the present invention utilize labeled magnetic nanoparticles and a unique "smart" magnetized collection needle.

According to yet another embodiment of the present invention special properties of labeled magnetic nanoparticles and a magnetized needle for collecting these particles after insertion into a biopsy site is described. The biopsy can be of any tissue for example the bone marrow, solid tumors or serum. Magnetic nanoparticles are labeled with molecules for targets of interest.

For example, paramagnetic or superparamagnetic nanoparticles are coated with specific biological coatings to attach to specific biological items including cancer cells, tumor cells, normal body cells, particular proteins, particular antibodies, particular viruses, neovascular structures, and microvascular structures. For example the nanoparticles are labeled with antibodies that target CD34 a cell surface marker that is more prevalent on the surface of leukemia cells than on normal leukocytes.

Magnetic fields of one embodiment of the present inventions produces force fields to attract the nanoparticles. Cell adhesion of the antibodies pull the cells with them.

Superparamagnetic nanoparticles have the property that, if no magnetic field is present, (a field smaller or comparable to the earth's field), the particles behave paramagnetically, i.e. they have a permeability close to one. However, in a relatively strong magnetic field, they become aligned with that field and exhibit ferromagnetism with permeabilities of several thousand, depending on the particle properties and the strength of the applied magnetic field. This very unusual property means that they can be injected into a volume when there is no applied field without congealing through their own magnetic attraction, but will be strongly attracted to regions of a large applied field. Other bio-materials in the area that are paramagnetic are not affected. Since it is known that millions of antibodies may attach to each cancer cell, a substantial magnetic moment occurs for the each cancer cell producing a significant attractive force in the presence of a large gradient magnetic field source.

Referring now to FIG. 1, the concept of a magnetic nanoparticle coated with an antibody is illustrated according to one embodiment of the present invention. Superparamagnetism considerably enhances the collection of cancer cells in a medium while also increasing cancer specificity through the use of a magnetic biopsy needle. According to one embodiment of the present invention, a magnetic needle biopsy comprises inserting a standard biopsy needle into the bone marrow, and withdrawing the inner rod to permit the injection of antibody-labeled magnetic nanoparticles through the opening of the biopsy needle. After waiting for a specified period, a magnetically tipped rod producing a strong magnetic field is inserted into the tube and left for a pre-determined collection time. The rod (also known as a wire) is removed with the cells containing the magnetic nanoparticles attached thereto. The nanoparticles are collected from the tip of the wire by either a strong magnetic field on the tip, or other mechanisms as described below. The material magnetic nanoparticles are subjected to a magnetic cell sorting process (for example MACS) and the sample is examined for cancer cells. Superparamagnetic properties of the particles also enhance the separation of unbound nanoparticles from those bound to cells.

A typical bone marrow biopsy needle, as currently used in standard biopsies, has a central removable rod with a pointed tip surrounded by an external tube is. The diameter of the central rod is about 1.2 mm. According to one embodiment of the present invention, the central removable rod is replaced by a magnetic rod or needle after initial insertion.

Figure 2:
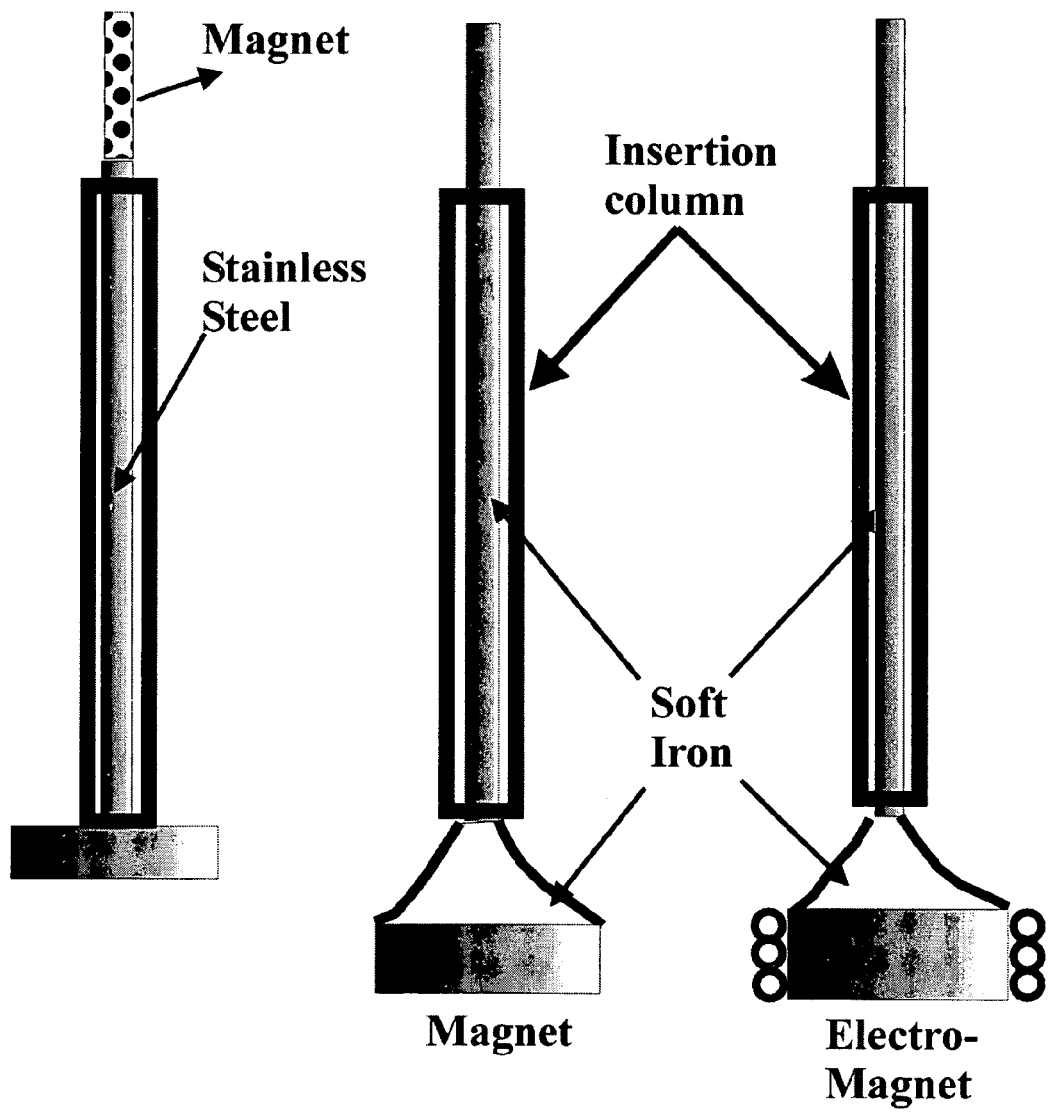
FIG. 2 illustrates three views (FIG. 2a, FIG. 2b, and FIG. 2C) of three magnetic biopsy devices according to different embodiments of the present invention.

Referring now to FIG. 2a, a tip of magnetic material of about 1 cm is located at one end of the central removable rod is illustrated according to another embodiment of the present invention. According to this configuration, magnetic material is located at tissue puncturing end of the rod at about the last cm of the central rod length. Magnetic material such as iron, or rare earth materials such as Knife, Smock, Ceramic, and Alnico are used in these magnetic rods. Magnetic field intensity maximums are about 4000 G for Ceramic 5 and about 13,000 G for Knife-42H with particular values of about 4000 G at the surface of the Knife magnets. The magnetic needle tip is of about one (1) mm diameter and about ten (10) mm length. The magnetic material maybe located at any position along the length of the rod. The dimension of the magnetic needle may range in diameter from about 0.5 mm to about 10 mm. The dimension of the magnetic needle may range in length from about 1 mm to about 1000 mm.

Referring now to FIG. 2b, a magnetic needle with a removable magnet is illustrated according to one embodiment of the present invention. This permits easy removal of the attached nanoparticles from the needle after extraction. In this embodiment, the needle, which is inserted into the biopsy tube, is conically enlarged as it extends beyond the housing of the tube wall or canola and proceeds outside and becomes physically in contact with a larger magnet. This structure permits a concentration of magnetic lines from the magnet located at one end of the rod along the length of the rod to the small tip at the opposing end.

The material and geometry concentrate the greatest flux possible to the tip. A rare earth magnet is attached to the large end so that its magnetic flux lines will proceed through the needle and are emitted at the tip end. In this embodiment of the present invention, large rare earth magnets are used at the end of the rod that is opposite the insertion point, which is not inserted into the patient. The external magnet is removed when the needle is extracted. In the absence of the magnetic field, the nanoparticles are removed from the needle by an additional external magnet extraction.

Referring now to FIG. 2c, an electromagnetic needle is illustrated according o one embodiment of the present invention. In this embodiment an electromagnetic coil wound around a ferromagnetic core and located at the end of the inserted magnetic needle produces the magnetic field. After completion of the biopsy, the external magnet field is turned off when the needle is extracted to remove the nanoparticles from the needle by an additional external magnet extraction.

According to yet another embodiment of the present invention, the biocompatibility of the needle (also known as a wire or rod) that is magnetizable is considered to avoid contact of rare earth magnetic material in the body. The needle material is coated with a thin biocompatible plastic coating to keep it from contacting the tissue. This coating also permits sterilization procedures and potential reuse of the needle.

In another embodiment of the present invention, one means for magnetizing the magnetizable rod is an external magnet. The external magnet is used to increase the magnetic force on the nanoparticles in the vicinity of the needle. The external magnetic pole may be either permanently magnetized or electromagnetic ally excited. The magnetic means can be located on the distal side of the biopsy site away from the biopsy site and used to amplify the collection efficiency of the magnetic rod. This magnetic circuit decreases the nanoparticles collection time at the needle. A rare earth or electromagnetic magnet is placed on the opposite side of the biopsy location to increase the magnetic divergence vector field at the needle location resulting in increase efficiency in collecting magnetic nanoparticles tagged cells. According to one embodiment of the present invention, the external magnet is similar to a commonly used C-magnet where in this case the C surrounds the limb to be biopsied and the needle is attached to one of the C-magnet faces. A knife magnet, or alternatively an electromagnetic coil giving field strength of 0.6 T generates the magnetic field.

Figure 3:
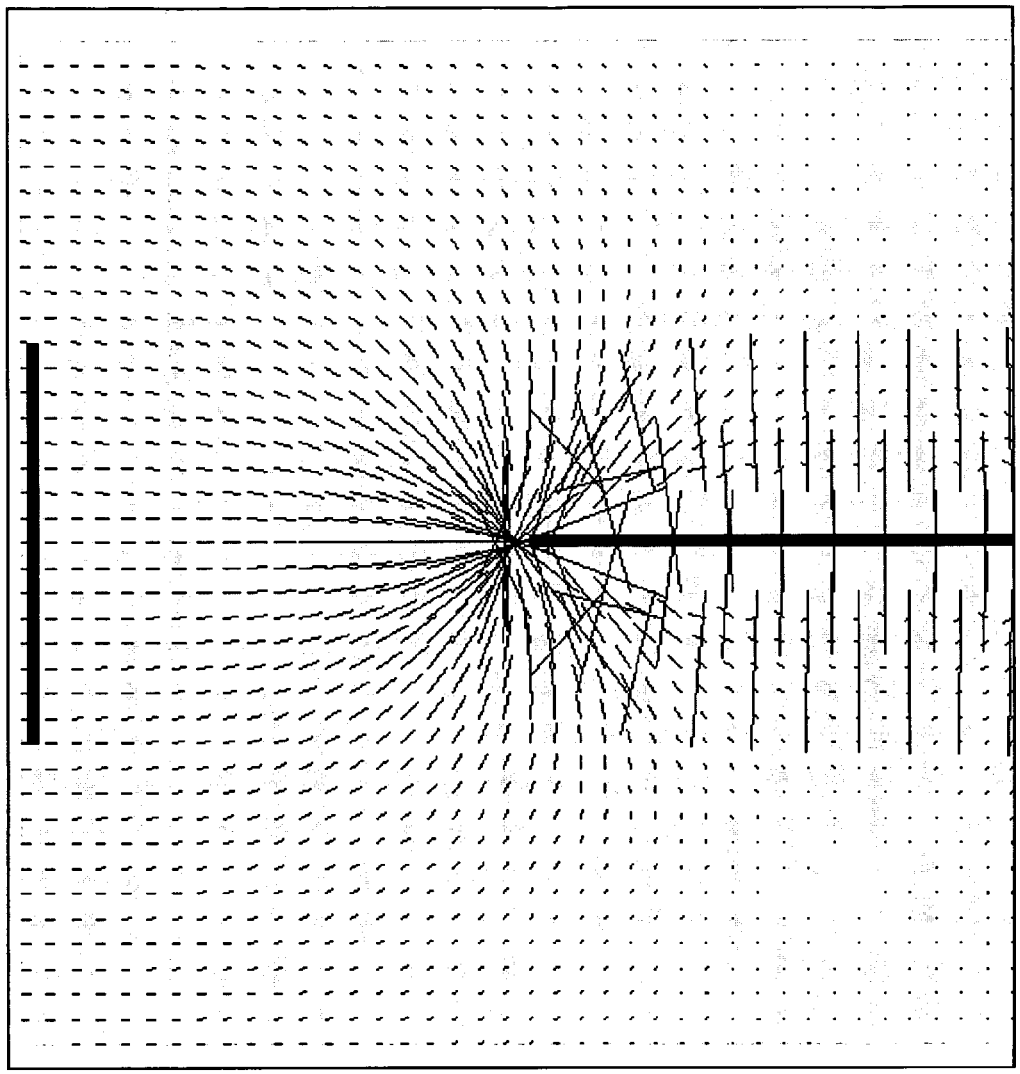
FIG. 3 is a calculation showing the magnetic fields in the vicinity of the magnetic needle.

FIG. 3 illustrates a magnetic field and the field derivatives of the magnetized needle extending to reasonable distances with the magnetizing fields from these magnets according to one embodiment of the present invention. Magnetic field strength from the needle versus distance from needle in a two (2) cm by two (2) cm box.

Figure 4:
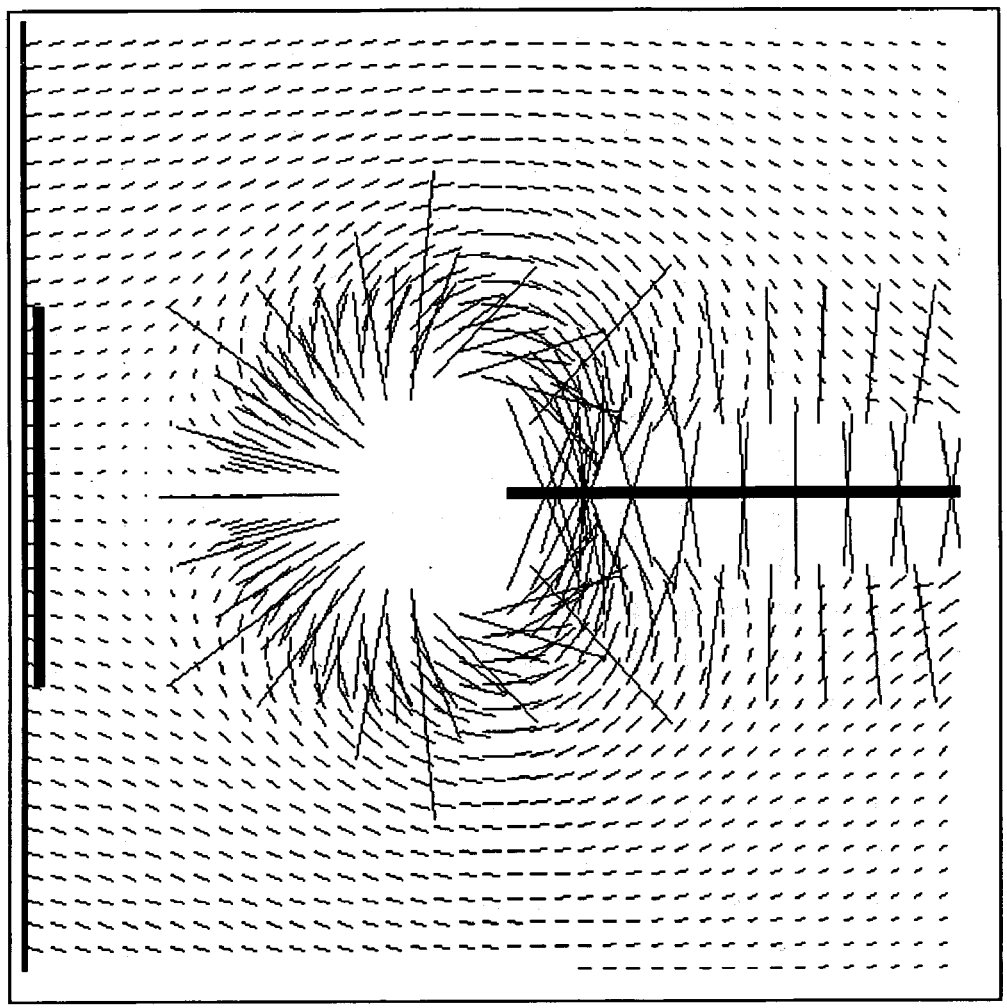
FIG. 4 is a calculation showing the force fields on magnetic nanoparticles in the vicinity of the magnetic needle.

Referring now to FIG. 4, the forces exerted on magnetic nanoparticles can be calculated using electromagnetic theory. Given that the viscosity of the medium is close to water and using Stokes theorem, it is possible to calculate the effective range of attraction and the time to pull the nanoparticles to the needle. Magnetic lines of force on magnetic nanoparticles from the magnetic needle in a two (2) cm by two (2) cm box.

Figure 5:
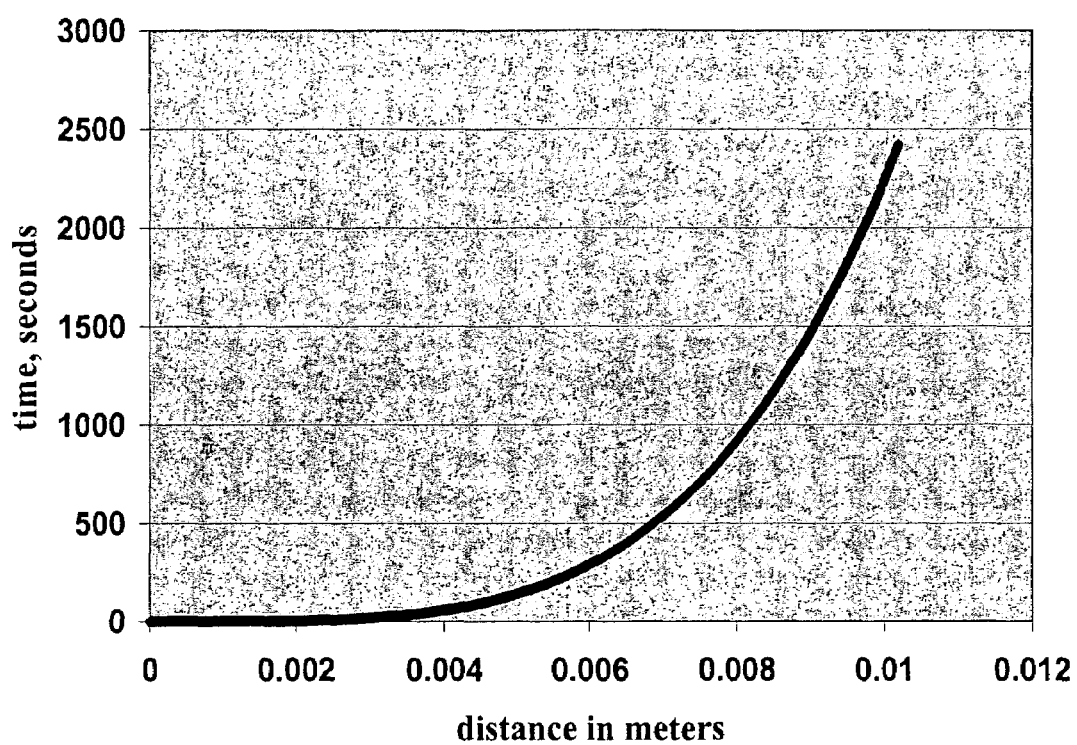
FIG. 5 is a calculation showing the time it takes to pull magnetic nanoparticles onto a magnetic biopsy device as a function of the magnetic nanoparticles initial distance from the needle when the biopsy device is inserted into the biopsy site according to one embodiment of the present invention.

Referring now to FIG. 5, detailed calculations of the forces, ranges, and collection times for various field strengths, needle configurations, and magnetic nanoparticles properties are illustrated in the graph. The time required to pull cells labeled with nanoparticles to the needle to provide the necessary guidance for collection times of the superparamagnetic particles are calculated according to one embodiment of the present invention.

Large number of magnetic nanoparticles attaches to each cell through the antibody mechanism and this adds considerably to the ability to attract the cells to the needle. For example, values of $2\times10^7$ nanoparticles per cell or 30 PG of superparamagnetic iron per cell are achievable. The range of the magnetic needle for attracting magnetic nanoparticles is calculated by modeling the magnetic needle used to collect the cells containing the nanoparticles as a magnetic dipole of dipole moment $\vec{m}$.

In practice, human cancer or other cells are obtained from bone marrow biopsies from clinical examinations of patients suspected of bone marrow disease or metastasis. Magnetically-labeled antibodies directed against CD34 (leukemia cells and myelodysplasia marker) and cytokeratin (breast cancer marker) are one example of nanoparticles utilized. The level of normal cells expressing cytokeratin in normal bone marrow is negligible, and the level of normal cells expressing CD34 is significantly below 1% in normal marrows. Since tumor involves levels upwards of 100% of the marrow, these markers will detect and sample tumor cells preferentially, if the tumor is present. This significantly increases the specificity of the bone marrow biopsy.

In another embodiment of the invention, magnetic guidance methods are used to analyze and treat tumors located at distant sites by guiding labeled paramagnetic or superparamagnetic nanoparticles from the biopsy insertion point to tumors located a sites removed from the biopsy site.

According to another embodiment of the present invention a magnetic biopsy apparatus is located at the end of a long catheter tube containing a wire instead of a magnetic tipped rod. The catheter containing the magnetic wire is guided to the area of interest, e.g. a tumor or cancer, and the central wire withdrawn. Magnetic nanoparticles, labeled with antibodies specific for the type of cancer suspected, are inserted into the tumor and then collected by reinsertion of the magnetic wire as they are in the biopsy method. The application is complex due to the effect of the steering magnets on the entire length of the wire and computer codes are used to control the magnetic steering fields.

A further embodiment of the magnetic biopsy needle approach is the direct injection of therapeutic agents into bone marrow. Upon identification of the type of cancer by the examination of the magnetically extracted cell type, anti-cancer agents are inserted into the existing biopsy site. Therapeutic drugs could also be injected directly into solid tumors using the magnetic guidance catheter method. Further enhancement would be obtained by attaching magnetic nanoparticles to the therapeutic agents and using the external field coils to further concentrate the particles in the tumor region according to yet another embodiment of the present invention.

In yet another embodiment of the present invention, the biopsy rod or needle has a channel that is formed by a portion of the cross-sectional area from the distal end of the biopsy rod to the proximal end of the biopsy rod being substantially hollow wherein nanoparticles are inserted into the magnetizable biopsy device for delivery to the subject and a biopsy site or a distant tumor location. Additionally, a catheter can be thread through the channel of the biopsy rod and into the subject wherein the catheter delivers nanoparticles to the biopsy site or distant tumor location.

Although the present invention has been described in terms of various exemplary embodiments for purposes of illustration, those of ordinary skill in the art will appreciate that various modifications and improvement may be made to the described embodiments without departing from the scope of the invention.

What is claimed is:

1. A method of obtaining from a patient a biopsy sample enriched for diseased cells comprising:
   injecting through a biopsy cannulae into a biopsy site of the patient superparamagnetic nanoparticles having a receptor for a specific target of interest of a diseased cell;
   incubating the superparamagnetic nanoparticles injected into the biopsy site within the patient to produce one or more superparamagnetic nanoparticle/diseased cell complexes when the target expressed on the surface of the diseased cell binds specifically to the receptor on the nanoparticle;
   placing a magnetizable rod through the cannulae and into the biopsy site such that the end of the magnetizable rod partially extends past the cannulae and into the biopsy site to collect superparamagnetic nanoparticle/diseased cell complexes directly form the biopsy site when the rod is magnetized;
   magnetizing the rod;
   removing from the cannulae the magnetized rod with the superparamagnetic nanoparticles/diseased cell complexes magnetically attached to the rod; and
   obtaining the biopsy sample enriched for diseased cells from the patient.

2. The method of claim 1 wherein the receptor on the superparamagnetic nanoparticles is an antibody.

3. The method of claim 1 wherein the diseased cells from a patient are in suspension.

4. The method according to claim 1 wherein superparamagnetic nanoparticles are guided to a location of a distant tumor through the use of external magnetic guidance.

5. The method according to claim 4 wherein the external magnetic guidance for the location of superparamagnetic nanoparticles is automated.

6. The method according to claim 1 wherein the biopsy sample is selected from bone marrow biopsy, tissue biopsy, serum biopsy and combinations thereof.

7. The method according to claim 1 wherein the diseased cell is selected from breast cancer cells, prostate cancer cells, ovarian cancer cells, lung cancer cells, liver cancer cells, lymphoma, and melanoma.

8. The method according to claim 1 wherein the superparamagnetic nanoparticles comprise a toxin or drug to destroy the diseased cell in the patient.

9. The method according to claim 1 wherein incubating is for a period of time of about 30 seconds to about 10 minutes.

10. The method according to claim 1 further comprising examining the biopsy sample enriched with the diseased cells using a microscope.

11. A method of obtaining from a patient a biopsy sample enriched for diseased cells comprising:
    injecting through a biopsy cannulae into a biopsy site of the patient superparamagnetic nanoparticles having a receptor for a specific target of interest of a diseased cell;
    incubating the superparamagnetic nanoparticles injected into the biopsy site within the patient to produce one or more superparamagnetic nanoparticle/diseased cell complexes when the target expressed on the surface of the diseased cell binds specifically to the receptor on the nanoparticle;
    placing a rod having a rare earth magnet at an end through the cannulae and into the biopsy site such that the end of the rod having the rare earth magnet partially extends past the cannulae and into the biopsy site to collect superparamagnetic nanoparticle/diseased cell complexes directly from the biopsy site;
    removing from the cannulae the rod with the superparamagnetic nanoparticles/diseased cell complexes magnetically attached to the rod; and
    obtaining the biopsy sample enriched for diseased cells from the patient.

12. The method of claim 11 wherein the receptor on the superparamagnetic nanoparticle is an antibody.

13. The method of claim 11 wherein the diseased cells from a patient are in suspension.

14. The method according to claim 11 wherein superparamagnetic nanoparticles are guided to a location of a distant tumor through the use of external magnetic guidance.

15. The method according to claim 11 wherein the external magnetic guidance for the location of superparamagnetic nanoparticles is automated.

16. The method according to claim 11 wherein the biopsy sample is selected from bone marrow biopsy, tissue biopsy, serum biopsy and combinations thereof.

17. The method according to claim 11 wherein the diseased cell is selected from breast cancer cells, prostate cancer cells, ovarian cancer cells, lung cancer cells, liver cancer cells, lymphoma, and melanoma.

18. The method according to claim 11 wherein the superparamagnetic particles are injected into the blood stream about one hour before the insertion of the magnetizable rod.

* * * * *